United States Patent
Sugimoto et al.

(10) Patent No.: US 11,576,819 B2
(45) Date of Patent: Feb. 14, 2023

(54) LAMINATE PATCHABLE TO LIVING BODY

(71) Applicant: NITTO DENKO CORPORATION, Osaka (JP)

(72) Inventors: Naoya Sugimoto, Osaka (JP); Ryoma Yoshioka, Osaka (JP); Eiji Toyoda, Osaka (JP)

(73) Assignee: NITTO DENKO CORPORATION, Osaka (JP)

( * ) Notice: Subject to any disclaimer, the term of this patent is extended or adjusted under 35 U.S.C. 154(b) by 278 days.

(21) Appl. No.: 16/333,441

(22) PCT Filed: Aug. 10, 2017

(86) PCT No.: PCT/JP2017/029070
§ 371 (c)(1),
(2) Date: Mar. 14, 2019

(87) PCT Pub. No.: WO2018/051695
PCT Pub. Date: Mar. 22, 2018

(65) Prior Publication Data
US 2019/0254880 A1 Aug. 22, 2019

(30) Foreign Application Priority Data
Sep. 15, 2016 (JP) .............................. JP2016-180361

(51) Int. Cl.
*A61F 13/00* (2006.01)
*A61F 13/02* (2006.01)
(Continued)

(52) U.S. Cl.
CPC ...... *A61F 13/0253* (2013.01); *A61F 13/0256* (2013.01); *A61K 9/70* (2013.01);
(Continued)

(58) Field of Classification Search
CPC .............. A61F 13/0253; A61F 13/0256; A61F 13/0259; A61K 9/70; A61K 9/7023;
(Continued)

(56) References Cited

U.S. PATENT DOCUMENTS 2,903,379 A * 9/1959 Norland ..................... C09J 7/50
428/335
6,210,704 B1 4/2001 Sasaki et al.
(Continued)

FOREIGN PATENT DOCUMENTS

AU 2014271258 B1 * 2/2016
CN 101220249 A 7/2008
(Continued)

OTHER PUBLICATIONS

Office Action, issued by the Japanese Patent Office dated Apr. 21, 2020, in connection with Japanese Patent Application No. 2016-180361.
(Continued)

*Primary Examiner* — Kim M Lewis
(74) *Attorney, Agent, or Firm* — Edwards Neils LLC; Jean C. Edwards, Esq.

(57) ABSTRACT

A laminate patchable to a living body and that includes a pressure-sensitive adhesive layer for patching to the living body, a substrate layer disposed on a one-side surface in a thickness direction of the pressure-sensitive adhesive layer and supporting the pressure-sensitive adhesive layer, and a protecting layer disposed on a one-side surface in the thickness direction of the substrate layer.

8 Claims, 1 Drawing Sheet

(51) Int. Cl.
*A61K 9/70* (2006.01)
*A61K 47/14* (2017.01)
*A61L 15/24* (2006.01)
*A61L 15/26* (2006.01)
*A61K 47/32* (2006.01)

(52) U.S. Cl.
CPC ............ *A61K 9/7023* (2013.01); *A61K 47/14* (2013.01); *A61K 47/32* (2013.01); *A61L 15/24* (2013.01); *A61L 15/26* (2013.01)

(58) Field of Classification Search
CPC ......... A61K 47/14; A61K 47/32; A61L 15/24; A61L 15/26; A61L 15/59
See application file for complete search history.

(56) References Cited

U.S. PATENT DOCUMENTS

| | | | |
|---|---|---|---|
| 2003/0224160 A1 | 12/2003 | Murakami et al. | |
| 2010/0217171 A1 | 8/2010 | Fukano et al. | |
| 2013/0004764 A1* | 1/2013 | Huang | C08J 7/042 428/424.4 |
| 2013/0184663 A1* | 7/2013 | Takada | A61F 13/00063 604/307 |
| 2014/0087207 A1* | 3/2014 | Zhao | B32B 15/08 428/623 |
| 2016/0299543 A1* | 10/2016 | Brooks | G06F 1/20 |
| 2019/0160797 A1* | 5/2019 | Sakairi | B32B 27/28 |

FOREIGN PATENT DOCUMENTS

| | | |
|---|---|---|
| CN | 101801322 A | 8/2010 |
| CN | 103252951 A | 8/2013 |
| EP | 3059290 A1 | 8/2016 |
| JP | S63-62123 U | 4/1988 |
| JP | H02-142434 U | 12/1990 |
| JP | H07-033646 A | 2/1995 |
| JP | 2000-201965 A | 7/2000 |
| JP | 2000-201966 A | 7/2000 |
| JP | 2000-201967 A | 7/2000 |
| JP | 2000-201969 A | 7/2000 |
| JP | 2003-081817 A | 3/2003 |
| JP | 2003-342541 A | 12/2003 |
| JP | 2007-020665 A | 2/2007 |
| JP | 2018043950 A * | 3/2018 ............. A61K 47/14 |
| JP | 6807196 B2 * | 1/2021 ............. A61K 47/14 |
| WO | WO-2012014585 A1 * | 2/2012 ......... A61F 13/0253 |
| WO | 2012/133727 A1 | 10/2012 |
| WO | WO-2013111773 A1 * | 8/2013 ............. B32B 27/08 |
| WO | WO-2017187437 A1 * | 11/2017 |

OTHER PUBLICATIONS

International Preliminary Report on Patentability issued by WIPO dated Mar. 19, 2019, in connection with International Patent Application No. PCT/JP2017/029070.
Office Action, issued by the State Intellectual Property Office dated Dec. 23, 2020, in connection with Chinese Patent Application No. 201780056032.5.
Extended European Search Report issued by the European Patent Office dated Apr. 8, 2020, in connection with European Patent Application No. 17850601.0.
Office Action, issued by the State Intellectual Property Office dated Jul. 13, 2021, in connection with Chinese Patent Application No. 201780056032.5.
Polymer Synthesis Technology, Feb. 2011, Version 1, East China University of Science and Technology Press, China.
Science of Pharmaceutical Excipients, Oct. 2008, First Edition, China Press of Traditional Chinese Medicine, Beijing.
Office Action, issued by the State Intellectual Property Office dated Dec. 16, 2021, in connection with Chinese Patent Application No. 201780056032.5.
International Search Report Issued in PCT/JP2017/029070 dated Sep. 26, 2017.
Written Opinion Issued in PCT/JP2017/029070 dated Sep. 26, 2017.

* cited by examiner

LAMINATE PATCHABLE TO LIVING BODY

CROSS-REFERENCE TO RELATED APPLICATIONS

The present application is a 35 U.S.C. 371 National Stage Entry of PCT/JP2017/029070, filed on Aug. 10, 2017, which claims priority from Japanese Patent Application No. 2016-180361, filed on Sep. 15, 2016, the contents of all of which are herein incorporated by reference in their entirety.

TECHNICAL FIELD

The present invention relates to a laminate patchable to a living body, to be specific, to a laminate patchable to a living body used for various uses such as medical use and sanitary material use.

BACKGROUND ART

Conventionally, it has been known that various pressure-sensitive adhesion tapes are used for medical use and sanitary material use. Those pressure-sensitive adhesion tapes are directly patched to the skin, so that they suppress physical stimuli given to the skin at the time of peeling, while having elasticity capable of conforming to a curved surface and movement of the skin.

For example, a pressure-sensitive adhesion sheet having a pressure-sensitive adhesion layer that is formed from a resin composition containing an acrylic ester polymer as a main component and a carboxylic acid ester added so as to be easily peeled from the skin on a film has been proposed (ref: for example, Patent Document 1).

CITATION LIST

Patent Document
Patent Document 1: Japanese Unexamined Patent Publication No. 2003-342541

SUMMARY OF THE INVENTION

Problem to be Solved by the Invention

However, in the pressure-sensitive adhesion sheet including Patent Document 1, a printed layer may be printed on a surface thereof in accordance with its use, and in such a case, printing resistance in accordance with a printing method is required.

Means for Solving the Problem

The present invention (1) includes a laminate patchable to a living body including a pressure-sensitive adhesive layer for patching to the living body, a substrate layer disposed on a one-side surface in a thickness direction of the pressure-sensitive adhesive layer and supporting the pressure-sensitive adhesive layer, and a protecting layer disposed on a one-side surface in the thickness direction of the substrate layer.

The laminate patchable to a living body includes the protecting layer that is disposed on the one-side surface in the thickness direction of the substrate layer, so that when the printed layer is printed, a transfer of a solvent used for forming the printed layer into the inside of the laminate patchable to a living body can be suppressed. Thus, a swelling of the laminate patchable to a living body can be suppressed, and deformation such as wrinkles can be suppressed. Or, damage caused by a friction of a printing device can be suppressed. Accordingly, the laminate patchable to a living body has excellent printing resistance.

The present invention (2) includes the laminate patchable to a living body described in (1), wherein the protecting layer is at least one of a chemical resistance layer and an abrasion resistance layer.

The laminate patchable to a living body has at least one of chemical resistance and abrasion resistance, so that the swelling of the laminate patchable to a living body can be suppressed, and the deformation such as wrinkles can be suppressed by the solvent used for forming the printed layer. Or, the damage caused by the friction of the printing device can be suppressed.

The present invention (3) includes the laminate patchable to a living body described in (1) or (2), wherein the protecting layer is a chemical resistance layer, and the absolute value ($|SP_{cover} - SP_{solvent}|$) of a difference between the SP value ($SP_{cover}$) of the chemical resistance layer and the SP value ($SP_{solvent}$) of a solvent used for forming a printed layer is 1.0 or more.

The laminate patchable to a living body can furthermore suppress the transfer of the solvent used for forming the printed layer into the inside of the laminate patchable to a living body, so that the swelling of the laminate patchable to a living body can be suppressed, and the deformation such as wrinkles can be further more surely suppressed. Accordingly, the laminate patchable to a living body has further more excellent printing resistance.

The present invention (4) includes the laminate patchable to a living body described in any one of (1) to (3), wherein the protecting layer is a chemical resistance layer, and the SP value ($SP_{cover}$) of the chemical resistance layer is 12.0 or more.

The laminate patchable to a living body can furthermore suppress the transfer of the solvent used for forming the printed layer into the inside of the laminate patchable to a living body, so that the swelling of the laminate patchable to a living body can be suppressed, and the deformation such as wrinkles can be further more surely suppressed. Accordingly, the laminate patchable to a living body has further more excellent printing resistance.

Effect of the Invention

The laminate patchable to a living body of the present invention has excellent printing resistance.

DESCRIPTION OF EMBODIMENTS

1. Layer Structure of Laminate Patchable to Living Body

Figure 1:
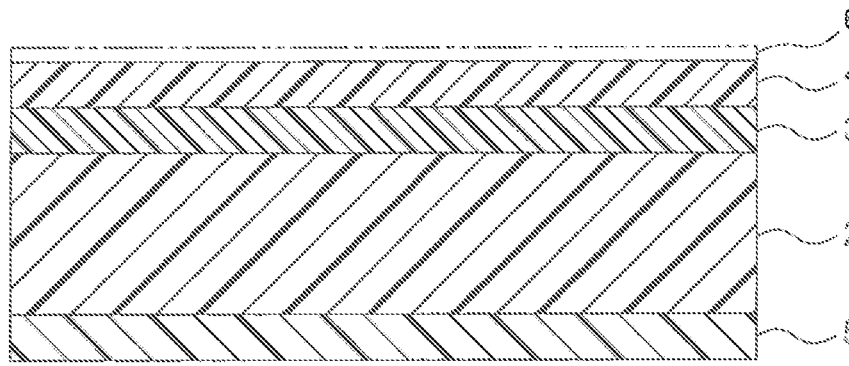
FIG. 1 shows a cross-sectional view of one embodiment (embodiment including a peeling layer) of a laminate patchable to a living body of the present invention.

As shown in FIG. 1, a laminate patchable to a living body 1 that is one embodiment of the present invention includes a pressure-sensitive adhesive layer 2, a substrate layer 3, and a protecting layer 4. The laminate patchable to a living body 1 also includes a peeling layer 5. To be specific, the laminate patchable to a living body 1 sequentially includes the peeling layer 5, the pressure-sensitive adhesive layer 2, the substrate layer 3, and the protecting layer 4 toward one side in a thickness direction. In the following, each layer is sequentially described.

2. Peeling Layer

The peeling layer 5 is the other-side layer in the thickness direction that forms the other-side surface in the thickness direction of the laminate patchable to a living body 1. The peeling layer 5 is a film that is used for fabricating the pressure-sensitive adhesive layer 2, and a peeling layer that protects the pressure-sensitive adhesive layer 2 before the use of the laminate patchable to a living body 1 and is peeled from the pressure-sensitive adhesive layer 2 at the time of the use of the laminate patchable to a living body 1.

The peeling layer 5 has a generally flat plate (sheet) shape extending in a plane direction (direction perpendicular to the thickness direction). Examples of the peeling layer 5 include resin films including polyester films such as polyethylene terephthalate (PET) film, polyethylene naphthalate film, and polybutylene terephthalate film and release paper such as wood free paper, craft paper, glassine paper, and topcoat paper. A surface of the peeling layer 5 may be subjected to peeling treatment.

The thickness of the peeling layer 5 is, for example, 1 μm or more, preferably 10 μm or more, and for example, 1000 μm or less, preferably 100 μm or less.

3. Pressure-Sensitive Adhesive Layer

The pressure-sensitive adhesive layer 2 is a patch layer for patching the substrate layer 3 to a living body. The pressure-sensitive adhesive layer 2 is in contact with the entire one-side surface in the thickness direction of the peeling layer 5. The pressure-sensitive adhesive layer 2 has a generally flat plate (sheet) shape extending in the plane direction. The pressure-sensitive adhesive layer 2 is prepared from a pressure-sensitive adhesive composition.

The pressure-sensitive adhesive composition contains, for example, an acrylic polymer. Preferably, the pressure-sensitive adhesive composition contains an acrylic polymer and a carboxylic acid ester.

The acrylic polymer is a main component in the pressure-sensitive adhesive composition, and is, for example, a pressure-sensitive adhesive component.

The acrylic polymer is a polymer obtained by polymerizing a monomer component containing a (meth)acrylate ester (to be specific, isononyl acrylate, methoxyethyl acrylate, or the like) as a main component (the content ratio thereof in the monomer component is 70 mass % or more and 99 mass % or less) and a monomer copolymerizable with the (meth)acrylate ester (to be specific, acrylic acid or the like) as an optional component (the content ratio thereof in the monomer component is 30 mass % or less and 1 mass % or more). An example of the acrylic polymer includes the acrylic polymer described in Japanese Unexamined Patent Publication No. 2003-342541.

The content ratio of the acrylic polymer with respect to the pressure-sensitive adhesive composition (the pressure-sensitive adhesive layer 2) is, for example, 80 mass % or less, preferably 70 mass % or less, and for example, 30 mass % or more, preferably 60 mass % or more.

The carboxylic acid ester in the pressure-sensitive adhesive composition is a pressure-sensitive adhesive force adjusting agent that reduces the pressure-sensitive adhesive force of the acrylic polymer and adjusts the pressure-sensitive adhesive force of the pressure-sensitive adhesive layer 2. The carboxylic acid ester is a carboxylic acid ester that is compatible with the acrylic polymer.

The carboxylic acid ester is, for example, an ester of a carboxylic acid and an alcohol.

An example of the carboxylic acid includes a fatty acid containing one carboxyl group in a molecule. Examples of the fatty acid include monocarboxylic acids including straight-chain saturated fatty acids having a carbon number of 5 or more and 22 or less such as valeric acid (pentanoic acid, carbon number of 5), caproic acid (hexanoic acid, carbon number of 6), enanthic acid (heptanoic acid, carbon number of 7), caprylic acid (octanoic acid, carbon number of 8), pelargonic acid (nonanoic acid, carbon number of 9), capric acid (decanoic acid, carbon number of 10), undecanoic acid (carbon number of 11), lauric acid (dodecanoic acid, carbon number of 12), myristic acid (tetradecanoic acid, carbon number of 14), palmitic acid (hexadecanoic acid, carbon number of 16), stearic acid (octadecanoic acid, carbon number of 18), and behenic acid (docosanoic acid, carbon number of 22); branched saturated fatty acids having a carbon number of 8 or more and 18 or less such as 2-ethyl hexanoic acid, dimethyloctanoic acid, and isostearic acid (2-heptyl undecanoic acid); and unsaturated fatty acids having a carbon number of 5 or more and 22 or less such as oleic acid, linolic acid, and linolenic acid.

Examples of the carboxylic acid also include polycarboxylic acids having two or more carboxyl groups in a molecule including dicarboxylic acids such as fumaric acid and phthalic acid. Furthermore, examples of the carboxylic acid include hydroxycarboxylic acids such as lactic acid.

As the carboxylic acid, preferably, a fatty acid having one carboxyl group in a molecule is used, more preferably, a straight-chain saturated fatty acid is used, further more preferably, a straight-chain saturated fatty acid having a carbon number of 6 or more and 18 or less is used, particularly preferably, a straight-chain saturated fatty acid having a carbon number of 8 or more and 16 or less is used, most preferably, a caprylic acid (carbon number of 8) is used.

Examples of the alcohol include monohydric alcohols and polyhydric alcohols.

Examples of the monohydric alcohol include methanol, ethanol, propanol, isopropanol, butanol, hexanol, octanol, decanol, cetyl alcohol (1-hexadecanol), isocetyl alcohol, myristyl alcohol (1-tetradecanol), and stearyl alcohol (1-octadecanol).

Examples of the polyhydric alcohol include dihydric alcohols such as ethylene glycol and propylene glycol, trihydric alcohols such as glycerin and trimethylolpropane, and tetrahydric alcohols such as pentaerythritol and diglycerine.

As the alcohol, preferably, a polyhydric alcohol is used, more preferably, a trihydric alcohol is used, further more preferably, a glycerin is used.

In the carboxylic acid ester, when the alcohol is the polyhydric alcohol, a portion of the hydroxyl group in the polyhydric alcohol forms an ester bond, and the remaining portion can also remain as the hydroxyl group.

To be specific, an example of the carboxylic acid ester includes an ester of a carboxylic acid (fatty acid) and a trihydric alcohol such as glyceryl tricaprylate, glyceryl monocaprylate, glyceryl tri-2-ethyl hexanoate, glyceryl tricaprate, glyceryl trilaurate, glyceryl triisostearate, glyceryl trioleate, and tri-2-ethylhexanoate trimethylolpropane. An example of the carboxylic acid ester also includes an ester of a carboxylic acid and a dihydric alcohol such as propylene glycol dicaprylate, propylene glycol dicaprate, and propylene glycol diisostearate. An example of the carboxylic acid ester also includes an ester of a carboxylic acid and a monohydric alcohol such as ethyl myristate, isopropyl myristate, isopropyl palmitate, butyl stearate, isopropyl isostearate, hexyl laurate, diethyl phthalate, dioctyl phthalate, stearyl myristate, stearyl oleate, cetyl dimethyloctanoate, cetyl 2-ethylhexanoate, isocetyl 2-ethylhexanoate, stearyl 2-ethylhexanoate, and dioctyl succinate. Furthermore, examples of the carboxylic acid ester include cetyl lactate and myristyl lactate.

As the carboxylic acid ester, preferably, an ester of a fatty acid and a trihydric alcohol is used, more preferably, in view of compatibility, an ester of a fatty acid and a glycerin (glyceryl trifatty acid ester and glyceride tricaprylate) is used, further more preferably, an ester of a straight-chain saturated fatty acid and a glycerin (tri[straight-chain fatty acid] glyceryl) is used, particularly preferably, a glyceryl tricaprylate is used.

When the carboxylic acid ester is the ester of the fatty acid and the trihydric alcohol, the number of ester group per molecule is, for example, 1 or more, preferably 2 or more, more preferably 3.

These carboxylic acid esters can be used alone or in combination of two or more. Preferably, the carboxylic acid ester is used alone.

The content ratio of the carboxylic acid ester with respect to 100 parts by mass of the acrylic polymer is, for example, 30 parts by mass or more, preferably 50 parts by mass or more, and for example, 100 parts by mass or less, preferably 70 parts by mass or less. The content ratio of the carboxylic acid ester with respect to the pressure-sensitive adhesive composition (the pressure-sensitive adhesive layer 2) is, for example, 20 mass % or more, preferably 30 mass % or more, and for example, 70 mass % or less, preferably 40 mass % or less.

The pressure-sensitive adhesive composition can also contain a cross-linking agent as needed. The cross-linking agent is a cross-linking component that cross-links an acrylic polymer. Examples of the cross-linking agent include polyisocyanate compound, epoxy compound, melamine compound, peroxide compound, urea compound, metal alkoxide compound, metal chelate compound, metal salt compound, carbodiimide compound, oxazoline compound, aziridine compound, and amine compound. These cross-linking agents can be used alone or in combination of two or more. As the cross-linking agent, preferably, a polyisocyanate compound (polyfunctional isocyanate compound) is used. The ratio of the cross-linking agent with respect to 100 parts by mass of the acrylic polymer is, for example, 0.001 parts by mass or more, preferably 0.01 parts by mass or more, and for example, 10 parts by mass or less, preferably 1 part by mass or less.

The thickness of the pressure-sensitive adhesive layer 2 is, for example, 1 μm or more, preferably 10 μm or more, and for example, 200 μm or less, preferably 80 μm or less.

4. Substrate Layer

The substrate layer 3 is disposed at one side in the thickness direction of the pressure-sensitive adhesive layer 2. To be specific, the substrate layer 3 is disposed on the entire one-side surface in the thickness direction of the pressure-sensitive adhesive layer 2. That is, the substrate layer 3 is in contact with the one-side surface in the thickness direction of the pressure-sensitive adhesive layer 2. The substrate layer 3 has a generally flat plate (sheet) shape extending in the plane direction. In this manner, the substrate layer 3 supports the pressure-sensitive adhesive layer 2. The substrate layer 3 is prepared from a substrate composition.

The substrate composition contains, for example, a substrate resin. Preferably, the substrate composition contains the substrate resin and the carboxylic acid ester.

The substrate resin is a main component in the substrate composition, and is, for example, a flexible resin that is capable of imparting appropriate elasticity, toughness, flexibility, and stretchability to the substrate layer 3.

The substrate resin is not particularly limited, and examples thereof include thermoplastic resins such as polyurethane resin, silicone resin, polystyrene resin, vinyl chloride resin, and polyester resin.

The content ratio of the substrate resin with respect to the substrate composition (the substrate layer 3) is, for example, 99 mass % or less, preferably 95 mass % or less, and for example, 70 mass % or more, preferably 80 mass % or more.

The carboxylic acid ester in the substrate composition is an elasticity adjusting agent for imparting the elasticity. As the carboxylic acid ester, the same carboxylic acid ester as that in the above-described pressure-sensitive adhesive composition is used, and of those, the carboxylic acid ester is appropriately selected in accordance with its use and purpose. As the carboxylic acid ester in the substrate composition, preferably, the same type of carboxylic acid ester as that in the pressure-sensitive adhesive composition is used. As the carboxylic acid ester in the substrate composition, preferably, a glyceryl trifatty acid ester is used. To be specific, preferably, both of the carboxylic acid ester in the substrate composition and that in the pressure-sensitive adhesive composition are the glyceryl trifatty acid ester.

These carboxylic acid esters can be used alone or in combination of two or more. Preferably, the carboxylic acid ester is used alone.

The content ratio of the carboxylic acid ester with respect to 100 parts by mass of the substrate resin is, for example, 1 part by mass or more, preferably 5 parts by mass or more, and for example, 50 parts by mass or less, preferably 25 parts by mass or less. The content ratio of the carboxylic acid ester with respect to the substrate composition (the substrate layer 3) is, for example, 1 mass % or more, preferably 5 mass % or more, and for example, 30 mass % or less, preferably 20 mass % or less.

The fracture elongation of the substrate layer 3 is, for example, 100% or more, preferably 200% or more, more preferably 300% or more, and for example, 2000% or less, preferably 1500% or less, more preferably 1000% or less. The measurement of the fracture elongation is described in Examples later. When the fracture elongation of the substrate layer 3 is within the above-described range, a reduction of the handling properties and a reduction of the strength can be suppressed. The fracture elongation of the substrate layer 3 is obtained by a method described in Examples later.

The moisture permeability of the substrate layer 3 is, for example, 300 (g/m$^2$/day) or more, preferably 600 (g/m$^2$/day) or more, further more preferably 1000 (g/m$^2$/day) or more. When the moisture permeability of the substrate layer 3 is the above-described lower limit or more, in a case where the laminate patchable to a living body 1 is patched to the living body, a load to the living body can be suppressed. The moisture permeability of the substrate layer 3 is obtained by the method described in Examples later.

The thickness of the substrate layer 3 is, for example, 1 μm or more, preferably 5 μm or more, and for example, 200 μm or less, preferably 50 μm or less.

When the thickness of the substrate layer 3 is the above-described lower limit or more, the shape of the substrate layer 3 can be surely retained. Thus, the laminate patchable to a living body 1 including the substrate layer 3 has excellent handleability. When the thickness of the substrate layer 3 is the above-described upper limit or less, the substrate layer 3 can be surely patched to the living body.

5. Protecting Layer

The protecting layer 4 is a protecting layer for suppressing the deformation and the damage of the laminate patchable to a living body 1 when a printed layer (a reference numeral 6 shown by a phantom line) is formed on the one-side surface (surface of the protecting layer) in the thickness direction of the laminate patchable to a living body 1 by printing. The protecting layer 4 is disposed at one side in the thickness direction of the substrate layer 3. To be specific, the protecting layer 4 is disposed on the entire one-side surface in the thickness direction of the substrate layer 3. That is, the protecting layer 4 is in contact with the one-side surface in the thickness direction of the substrate layer 3. The protecting layer 4 has a generally flat plate (sheet) shape extending in the plane direction.

Examples of the protecting layer 4 include a chemical resistance layer and an abrasion resistance layer.

5-1. Chemical Resistance Layer

The chemical resistance layer is a lubrication suppressing layer that suppresses the swelling and the deformation of the laminate patchable to a living body 1 (to be specific, the chemical resistance layer and the substrate layer 3) by a solvent contained in ink (printing liquid) used at the time of the printing. To be specific, the chemical resistance layer is, for example, a layer in which the appearance of the surface thereof does not change or seldom changes (such a degree that 80% or more of the contact area does not change) at the time of the contact with the solvent (preferably, diethylene glycol monoethyl ether acetate) for 10 minutes in JIS K 7114 (Plastics-Methods of test for the determination of the effects of immersion in liquid chemicals).

The chemical resistance layer is, for example, formed from a protecting composition containing a resin. Examples of the resin used for the chemical resistance layer include polyvinyl alcohol, cross-linked product of the polyvinyl alcohol, copolymer of the polyvinyl alcohol, modified product of the polyvinyl alcohol, poly(meth)acrylic acid, poly(meth)acrylate, silicone resin, and an amino group-containing (meth)acrylate ester polymer cross-linked with an epoxy resin.

As the resin of the chemical resistance layer, in view of chemical resistance, preferably, a polyvinyl alcohol, a cross-linked product of the polyvinyl alcohol, a copolymer of the polyvinyl alcohol, and a modified product of the polyvinyl alcohol are used, more preferably, a polyvinyl alcohol and a cross-linked product of the polyvinyl alcohol are used.

The polyvinyl alcohol (PVA) is a hydrolysate (to be specific, partial hydrolysate) of the polyvinyl acetate. The polyvinyl alcohol is a water-soluble polymer.

A saponification degree of the polyvinyl alcohol is, for example, 80 mol % or more, preferably 90 mol % or more, more preferably 95 mol % or more, and for example, 100 mol % or less. By setting the saponification degree within the above-described range, the chemical properties can be furthermore improved.

A polymerization degree of the polyvinyl alcohol is, for example, 1000 or more, preferably 1500 or more, more preferably 1800 or more, and for example, 10000 or less, preferably 5000 or less, more preferably 3000 or less. By setting the polymerization degree within the above-described range, the chemical properties can be furthermore improved.

The viscosity of a 4 mass % aqueous solution (20° C.) of the polyvinyl alcohol is, for example, 5 mPa·s or more, preferably 10 mPa·s or more, and for example, 100 mPa·s or less, preferably 50 mPa·s or less.

The saponification degree, the polymerization degree, and the viscosity of the polyvinyl alcohol are calculated in accordance with "Testing methods for polyvinyl alcohol" described in JIS K 6726 (1994).

The cross-linked product of the polyvinyl alcohol is obtained by cross-linking the polyvinyl alcohol by using a cross-linking agent.

Examples of the cross-linking agent include isocyanate compound, oxazoline compound, melamine compound, epoxy compound, carboxylic acid compound, carboxylic acid anhydride, carbodiimide compound, bisvinylsulfone compound, organic titanium compound, zirconium compound, and boron compound. In view of chemical resistance and abrasion resistance, preferably, an isocyanate compound, an organic titanium compound, and a bisvinylsulfone compound are used, more preferably, an isocyanate compound and an organic titanium compound are used, further more preferably, an isocyanate compound is used.

As the isocyanate compound, for example, a blocked isocyanate compound that is obtained by blocking the isocyanate group is also included. To be specific, examples of the blocked isocyanate compound include the MEIKANATE series, the SU series, the DM series, and the NBP series manufactured by Meisei Chemical Works, Ltd.

Examples of the organic titanium compound include titanium lactate, titanium lactate ammonium salt, and titanium triethanol aminate.

Examples of the bisvinylsulfone compound include N—N'-ethylenebis[2-(vinylsulfonyl)acetoamide] and N—N'-trimethylene[2-(vinylsulfonyl)acetoamide].

The cross-linked product of the polyvinyl alcohol is produced by blending the polyvinyl alcohol with the cross-linking agent to then progress a cross-linking reaction by heating. The mixing ratio of the cross-linking agent with respect to 100 parts by mass of the polyvinyl alcohol is, for example, 1 part by mass of more, preferably 5 parts by mass or more, more preferably 10 parts by mass or more, and for example, below 50 parts by mass, preferably 35 parts by mass or less, more preferably 20 parts by mass or less.

The copolymer of the polyvinyl alcohol is obtained by copolymerizing a vinyl acetate and a comonomer and then converting an acetic acid group into a hydroxyl group by saponification reaction. Examples of the comonomer used at this time include olefin such as ethylene, (meth)acrylate ester, and (meth)acrylate amide.

The modified product of the polyvinyl alcohol is obtained by bonding a functional group such as alkyl group, ester group, amide group, acetoacetyl group, and silyl group to the hydroxyl group of the polyvinyl alcohol.

The protecting composition can, for example, contain an additive such as surfactant in accordance with its use and purpose. The surfactant is a coating property improver that improves the coating properties of the resin in the protecting composition. An example of the surfactant includes a polyether-modified silicone. The addition ratio of the additive (surfactant) with respect to 100 parts by mass of the resin is, for example, 0.01 parts by mass or more, preferably 0.1 parts by mass or more, and for example, 10 parts by mass or less, preferably 5 parts by mass or less.

The SP value ($SP_{cover}$) of the chemical resistance layer is, for example, 10.0 or more, preferably 11.0 or more, more preferably 12.0 or more, and for example, 16.0 or less, preferably 14.0 or less. When the SP value of the chemical resistance layer is within the above-described range, the transfer of the solvent used for forming the printed layer 6 into the inside of the chemical resistance layer (the protecting layer 4) and the swelling thereof can be effectively prevented.

The SP value is calculated based on the Fedors method. To be specific, by imputing a structure of the resin contained in the protecting layer such as the chemical resistance layer into an analytical software such as HSPiP, the SP value is obtained. Or, the SP value can be also obtained based on the literature value that is already calculated by the Fedors method.

The absolute value ($|SP_{cover}-SP_{solvent}|$) of a difference between the SP value ($SP_{cover}$) of the chemical resistance layer and the SP value ($SP_{solvent}$) of the solvent used for forming the printed layer 6 is set so as to be, for example, 1.0 or more, preferably 2.0 or more, more preferably 3.0 or more, further more preferably 3.5 or more, and for example, 7.0 or less, preferably 5.0 or less, more preferably 4.0 or less. When the absolute value is within the above-described range, the transfer of the solvent into the inside of the chemical resistance layer (the protecting layer 4) and the swelling thereof can be effectively suppressed.

An example of the solvent used for forming the printed layer 6 includes an organic solvent. Examples of the organic solvent include aromatic hydrocarbon solvents such as toluene and xylene; ester solvents such as ethyl acetate, acetic acid, n-propyl, diethylene glycol monoethyl ether acetate; ketone solvents such as methyl ethyl ketone and methyl isobutyl ketone; and alcohol solvents such as methanol, ethanol, isopropyl alcohol, and 1-methoxy-2-propanol. Preferably, an ester solvent is used, more preferably, a diethylene glycol monoethyl ether acetate is used.

The SP value (SPsolvent) of the solvent is appropriately set in accordance with the type and the printing method of the printed layer 6, and is, for example, 7.0 or more, preferably 8.0 or more, more preferably 9.0 or more, and for example, 13.0 or less, preferably 10.0 or less.

5-2. Abrasion Resistance Layer

The abrasion resistance layer is a layer that suppresses the damage of the one-side surface in the thickness direction of the laminate patchable to a living body 1 (to be specific, the surface of the chemical resistance layer) caused by the contact with a printing device such as applicator at the time of the printing. To be specific, the abrasion resistance layer is, for example, a layer in which the appearance of the surface thereof does not change or seldom changes (for example, such a degree that a small scar is recognized) in the measurement of JIS K 5600-5-4 (Mechanical property of film, Scratch hardness (Pencil method), Pencil hardness B).

The abrasion resistance layer is, for example, formed from a protecting composition containing a resin. Examples of the resin used for the abrasion resistance layer include epoxy resin, cross-linked product of the polyvinyl alcohol, copolymer of the polyvinyl alcohol, and modified product of the polyvinyl alcohol. Preferably, an epoxy resin and a cross-linked product of the polyvinyl alcohol are used.

Examples of the epoxy resin include aromatic epoxy resin, aliphatic-alicyclic epoxy resin, nitrogen-containing cyclic epoxy resin, glycidyl ether epoxy resin, dimer acid-modified epoxy resin, and urethane-modified epoxy resin.

Examples of the aromatic epoxy resin include bisphenol epoxy resins such as bisphenol A epoxy resin, bisphenol F epoxy resin, bisphenol S epoxy resin, and a modified product thereof; novolak epoxy resins such as phenol novolak epoxy resin and cresol novolak epoxy resin; diaminodiphenylmethane epoxy resins; naphthalene epoxy resins; and biphenyl epoxy resins.

Examples of the aliphatic-alicyclic epoxy resin include hydrogenated bisphenol A epoxy resin and dicyclo epoxy resin.

Examples of the nitrogen-containing cyclic epoxy resin include triglycidyl isocyanurate epoxy resin and hydantoin epoxy resin.

When the protecting composition contains the epoxy resin, preferably, a curing catalyst is further contained.

The curing catalyst is a catalyst that cures the epoxy resin, and examples thereof include imidazole compound, triphenylphosphine compound, triphenylborane compound, amino group-containing compound, and acid anhydride compound. Preferably, an imidazole compound is used.

Examples of the imidazole compound include 2-phenyl imidazole, 2-ethyl-4-methyl imidazole, 2-methyl imidazole, 2-undecyl imidazole, 2-phenyl-1H-imidazole4,5-dimethanol, and 2,4-diamino-6-(2'-methylimidazolyl (1)')ethyl-s-triazineisocyanuric acid adduct.

The mixing ratio of the curing catalyst with respect to 100 parts by mass of the epoxy resin is, for example, 0.01 parts by mass or more, preferably 0.1 parts by mass or more, and for example, 10 parts by mass or less, preferably 5 parts by mass or less.

The protecting composition in the abrasion resistance layer can also, for example, contain an additive such as surfactant.

In the present invention, as the protecting layer 4, preferably, a chemical resistance and abrasion resistance layer is used. That is, preferably, the protecting layer 4 has both chemical resistance and abrasion resistance. As the resin that forms a layer capable of having excellent chemical resistance and excellent abrasion resistance, preferably, a cross-linked product of the polyvinyl alcohol is used. That is, preferably, the protecting layer 4 is formed from a cross-linked product of the polyvinyl alcohol.

The thickness of the protecting layer 4 is, for example, 0.01 μm or more, preferably 0.1 μm or more, and for example, 20 μm or less, preferably 10 μm or less.

The ratio (thickness of the protecting layer 4/thickness of the substrate layer 3) of the thickness of the protecting layer 4 to that of the substrate layer 3 is, for example, 0.01 or more, preferably 0.05 or more, and for example, 0.50 or less, preferably 0.20 or less.

When the thickness of the protecting layer 4 is the above-described upper limit or less, the elasticity of the laminate patchable to a living body 1 can be retained. When the thickness of the protecting layer 4 is the above-described lower limit or more, the swelling and the friction at the time of the formation of the printed layer 6 can be more effectively prevented by the protecting layer 4.

6. Fabrication Method of Laminate Patchable to Living Body

To fabricate the laminate patchable to a living body 1, first, the plurality of peeling layers 5 are prepared. Subsequently, each of the pressure-sensitive adhesive layer 2 and the substrate layer 3 is fabricated on the surface of each of the peeling layers 5.

To fabricate the pressure-sensitive adhesive layer 2, first, the pressure-sensitive adhesive composition is prepared. To be specific, for example, the acrylic polymer and, if necessary, the carboxylic acid ester, and the cross-linking agent are blended to be mixed, so that the pressure-sensitive adhesive composition (pressure-sensitive adhesive layer coating liquid) is prepared. Next, the pressure-sensitive adhesive composition is applied to the surface of the peeling layer 5 to be subsequently dried by heating. The drying temperature is, for example, 100° C. or more and 140° C. or less, and the drying time is, for example, 1 minute or more and 15 minutes or less.

Thereafter, when the pressure-sensitive adhesive composition contains the cross-linking agent or the like, the dried pressure-sensitive adhesive composition is further heated (aged). The aging temperature is, for example, 40° C. or more and 80° C. or less, and the aging time is, for example, 1 hour or more and 100 hours or less.

In this manner, the pressure-sensitive adhesive layer 2 is fabricated on the surface of the peeling layer 5.

Separately, the substrate layer 3 is fabricated. To fabricate the substrate layer 3, a substrate composition is prepared. To be specific, for example, the substrate resin, the solvent, and if necessary, the carboxylic acid ester are blended to be mixed, so that a solution of the substrate composition (substrate coating liquid) is prepared. The solvent used for the substrate coating liquid is not particularly limited, and for example, organic solvents including ketone solvents such as methyl ethyl ketone and aprotic polar solvents such as dimethylformamide are used. These solvents can be used alone or in combination of two or more. When the substrate resin is prepared as a solution obtained by being dissolved in the solvent in advance, the solvent contained in the above-described solution is used as it is, and the substrate coating liquid may be prepared without separately adding the solvent.

Next, the substrate coating liquid is applied to the surface of the peeling layer 5. After the application, the substrate coating liquid is dried.

The drying temperature is, for example, 100° C. or more and 140° C. or less. The drying time is, for example, 1 minute or more and 15 minutes or less.

In this manner, the substrate layer 3 is fabricated on the surface of the peeling layer 5.

Thereafter, the pressure-sensitive adhesive layer 2 and the substrate layer 3 are stuck to each other by, for example, a laminator or the like. To be specific, the pressure-sensitive adhesive layer 2 and the substrate layer 3 are brought into contact with each other. Thereafter, the peeling layer 5 at the side of the substrate layer 3 is peeled.

In this manner, a laminate including the peeling layer 5, the pressure-sensitive adhesive layer 2, and the substrate layer 3 is fabricated.

Next, the protecting layer 4 is fabricated. To fabricate the protecting layer 4, first, the protecting composition is prepared. To be specific, for example, the resin, the solvent, and if necessary, the cross-linking agent and the surfactant are blended to be mixed, so that the protecting composition (the protecting layer coating liquid) is prepared.

Examples of the solvent used for the protecting layer coating liquid include aqueous solvents such as water in addition to the solvent used for the substrate coating liquid. When the resin is prepared as a solution obtained by being dissolved in the solvent in advance, the solvent contained in the above-described solution is used as it is, and the cross-linking agent, and furthermore, if necessary, the surfactant can be blended with the solution. As the mixing ratio of the solvent, the content ratio of the resin with respect to the protecting layer coating liquid is adjusted so as to be, for example, 1 mass % or more, preferably 5 mass % or more, and for example, 75 mass % or less, preferably below 50 mass %.

Next, the protecting composition is applied to the surface of the peeling layer 5 to be subsequently dried by heating. The drying temperature is, for example, 80° C. or more and 120° C. or less, and the drying time is, for example, 1 minute or more and 15 minutes or less.

Thereafter, when the protecting composition contains the cross-linking agent or the like, the dried protecting composition is further heated (aged). In this manner, the resin of the polyvinyl alcohol is cross-linked by the cross-linking agent, so that the cross-linked product is fabricated. The aging temperature is, for example, 110° C. or more and 150° C. or less, and the aging time is, for example, 1 minute or more and 15 minutes or less.

In this manner, the protecting layer 4 is fabricated on the surface of the peeling layer 5.

Thereafter, the laminate and the protecting layer 4 are stuck to each other by, for example, the laminator or the like. To be specific, the substrate layer 3 and the protecting layer 4 of the laminate are brought into contact with each other. Subsequently, the peeling layer 5 at the side of the protecting layer 4 is peeled.

In this manner, the laminate patchable to a living body 1 including the peeling layer 5, the pressure-sensitive adhesive layer 2, the substrate layer 3, and the protecting layer 4 is obtained.

7. Modified Examples

In the above-described one embodiment, as shown in FIG. 1, the laminate patchable to a living body 1 includes the peeling layer 5 in addition to the pressure-sensitive adhesive layer 2, the substrate layer 3, and the protecting layer 4.

Figure 2:
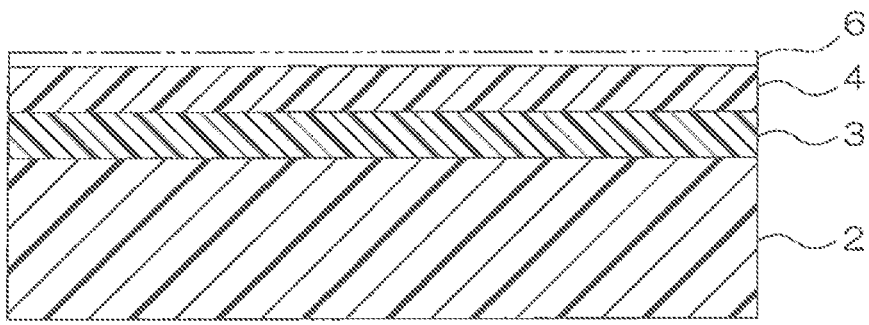
FIG. 2 shows a cross-sectional view of a modified example (embodiment without including a peeling layer) of the laminate patchable to a living body shown in FIG. 1.

As shown in FIG. 2, however, the laminate patchable to a living body 1 can also include only the pressure-sensitive adhesive layer 2, the substrate layer 3, and the protecting layer 4 without including the peeling layer 5 (ref: FIG. 1). The laminate patchable to a living body 1 shown in FIG. 2 is a three-layer laminate consisting of the pressure-sensitive adhesive layer 2, the substrate layer 3, and the protecting layer 4.

In the above-described one embodiment, as shown in FIG. 1, the laminate patchable to a living body 1 includes the pressure-sensitive adhesive layer 2, the substrate layer 3, and the protecting layer 4. The laminate patchable to a living body 1 can also further include, for example, the printed layer 6 such as ink layer and circuit layer. That is, in the modified example, the laminate patchable to a living body 1 preferably includes the printed layer 6 that is disposed on the one-side surface in the thickness direction of the protecting layer 4.

Examples of the printing method in the case where the above-described printed layer 6 is provided include known printing methods such as gravure printing, screen printing, flexo printing, air knife coating, and blade coating.

An example of the ink layer includes a laser marking ink layer described in WO 2012/008278.

8. Use of Laminate Patchable to Living Body

The laminate patchable to a living body 1 is used for patching to the living body.

The living body is not particularly limited. Examples of the living body include animal body and plant body. Examples of the animal body include human body (human); domestic animals such as cow, horse, pig, chicken, dog, and cat; and fish. Examples of the plant body include grains such as rice, barley, wheat, corn, and sugarcane; crops that form root stocks or tuberous roots such as potato and sweet potato; leguminous plants such as soybean, kidney bean, broad bean, and garden pea; seed plants such as peanut, sesame, rapeseed, cotton seed, sunflower, and safflower; and crops having a fruit such as apple, melon, and grapes. As the living body, preferably, an animal body is used, more preferably, a human body is used.

The laminate patchable to a living body 1 is, for example, used for various uses including medical use and sanitary material use, and to be specific, is used as a bandage or the like.

To be specific, when the laminate patchable to a living body 1 includes the peeling layer 5, first, the peeling layer 5 is peeled from the pressure-sensitive adhesive layer 2, and subsequently, the other-side surface in the thickness direction of the pressure-sensitive adhesive layer 2 is patched to the living body. To be specific, the substrate layer 3 is patched to the living body via the pressure-sensitive adhesive layer 2.

9. Function and Effect of Laminate Patchable to Living Body

The laminate patchable to a living body 1 may be required to have excellent printing resistance.

To be specific, when the above-described printed layer 6 is provided in the laminate patchable to a living body 1, for example, in a wire layer of a wearable device or the like, excellent printing resistance of not easily deforming the wire layer (for example, easily forming a desired-shaped wire layer) is required at the time of the formation of the wire. An example of the wearable device includes a living body patch-type sensor including a stretchable main body portion and a stretchable electronic circuit described in Japanese Translation of PCT International Application Publication No. 2012-508984.

In the ink layer in the laser marking film described in WO 2012/008278 or the like, for example, laser marking images showing various information such as bar codes and characters need to be clearly read. Thus, excellent printing resistance of not easily deforming the ink layer (for example, easily forming a clear ink layer) is required at the time of the formation of the ink layer.

However, the pressure-sensitive adhesion sheet described in Patent Document 1 consists of the film and the pressure-sensitive adhesion layer. Thus, there is a disadvantage that when the printed layer such as the ink layer is printed in the film, the solvent in the ink is transferred into the film, and the film swells based on the transfer, so that the deformation such as wrinkles occurs in the film. Or, there is a disadvantage that at the time of the printing, the printing device is brought into direct contact with the surface of the film, and the film is damaged by the friction.

Meanwhile, in one embodiment, the laminate patchable to a living body 1 includes the protecting layer 4 at one side in the thickness direction, so that excellent printing resistance is achieved.

When the laminate patchable to a living body 1 includes the chemical resistance layer as the protecting layer 4, in particular, in a case where the printed layer such as the ink layer is printed in the one-side surface in the thickness direction of the laminate patchable to a living body 1 (to be specific, the surface of the chemical resistance layer), the transfer of the solvent of the ink into the inside (the protecting layer 4 and the substrate layer 3) of the laminate patchable to a living body 1 is suppressed. Thus, the swelling of the laminate patchable to a living body 1 is suppressed, and the deformation such as wrinkles can be suppressed. Thus, in this case, the laminate patchable to a living body 1 has excellent chemical resistance.

When the laminate patchable to a living body 1 includes the abrasion resistance layer as the protecting layer 4, in a case where the ink layer or the like is printed in the one-side surface in the thickness direction of the laminate patchable to a living body 1 (to be specific, the surface of the abrasion resistance layer), the damage caused by the friction of the printing device can be suppressed. Thus, in this case, the laminate patchable to a living body 1 has excellent abrasion resistance.

EXAMPLES

Next, the present invention is further described based on Examples and Comparative Example. The present invention is however not limited by the following Examples and Comparative Example. The specific numerical values in mixing ratio (content ratio), property value, and parameter used in the following description can be replaced with upper limit values (numerical values defined as "or less" or "below") or lower limit values (numerical values defined as "or more" or "above") of corresponding numerical values in mixing ratio (content ratio), property value, and parameter described in the above-described "DESCRIPTION OF EMBODIMENTS".

Example 1

1. Fabrication of Pressure-Sensitive Adhesive Layer

In accordance with the description of Example 1 in Japanese Unexamined Patent Publication No. 2003-342541, an acrylic polymer was prepared from an isononyl acrylate (iNA), a methoxyethyl acrylate (MEA), and an acrylic acid (AA).

Next, 100 parts by mass of acrylic polymer, 60 parts by mass of glyceryl tricaprylate, and 0.01 parts by mass of Coronate HL (trade name, polyfunctional isocyanate compound, manufactured by Nippon Polyurethane Industry Co., Ltd.) as a cross-linking agent were blended to be stirred and mixed, so that a pressure-sensitive adhesive layer coating liquid (pressure-sensitive adhesive composition) was prepared. Thereafter, the pressure-sensitive adhesive layer coating liquid was applied to the surface of a PET film (peeling layer, thickness of 50 μm) in which the surface thereof was subjected to peeling treatment to be thereafter dried at 120° C. for 3 minutes, and the applied surface was further aged at 60° C. for 72 hours. In this manner, the pressure-sensitive adhesive layer 2 that was supported by the peeling layer 5 was fabricated. The thickness of the pressure-sensitive adhesive layer 2 was 25 μm.

2. Fabrication of Substrate Layer

A polyether urethane solution (trade name: "T-8180N", 20 mass % solution of polyether urethane (solvent=methyl ethyl ketone:dimethylformamide=1:1), manufactured by DIC Covestro Polymer Ltd.) and the glyceryl tricaprylate were blended at a normal temperature so that the mass ratio of the polyether urethane to the glyceryl tricaprylate was 100/10 to be then stirred and mixed, so that a substrate layer coating liquid was prepared. Thereafter, the substrate layer coating liquid was applied to the surface of the PET film (peeling layer) in which the surface thereof was subjected to peeling treatment to be then dried at 120° C. for 5 minutes. In this manner, the substrate layer 3 that was supported by the peeling layer was fabricated. The thickness of the substrate layer 3 was 8 μm.

In the substrate layer 3 from which the peeling layer was peeled, the fracture elongation of the substrate layer 3 was measured at a tensile rate of 5 mm/min with a test piece type 2 in conformity with JIS K 7127 (1999), and the result was 600%.

In the substrate layer 3 from which the peeling layer was peeled, the moisture permeability of the substrate layer 3 was measured under the condition A in conformity with JIS Z 0208 (1976), and the result was 2540 (g/m²/day).

3. Fabrication of Protecting Layer

A protecting layer coating liquid was prepared by blending, stirring and mixing 28.8 parts by mass (2.88 parts by mass as solid content) of 10 mass % aqueous solution of polyvinyl alcohol (trade name: "VF-20", saponification degree of 97.7 to 98.5 mol %, polymerization degree of 2000, the viscosity in the 4 mass % aqueous solution (20° C.) of 35 to 45 mPa·s, manufactured by JAPAN VAM & POVAL CO., LTD.), 1.07 parts by mass (0.47 parts by mass as solid content) of blocked isocyanate aqueous solution (trade name: "SU-268A", aqueous cross-linking agent, manufactured by Meisei Chemical Works, Ltd.) as a cross-linking agent, 0.02 parts by mass (solid content) of silicone surfactant (trade name: "SILFACE SAG 002", manufactured by Nissin Chemical Industry Co., Ltd.) as a surfactant, and 10.10 parts by mass of water.

Next, the protecting layer coating liquid was applied to the surface of a PET film (peeling layer) in which the surface thereof was subjected to peeling treatment to be thereafter dried under the conditions of 100° C. for 10 minutes. Thereafter, the applied surface was heated at 130° C. for 10 minutes to be subjected to cross-linking treatment. In this manner, the protecting layer 4 that was supported by the peeling layer 5 and prepared from the cross-linked product of the polyvinyl alcohol was fabricated. The thickness of the protecting layer 4 was 0.5 μm.

4. Fabrication of Laminate Patchable to Living Body

The pressure-sensitive adhesive layer 2 and the substrate layer 3 were stuck to each other at 60° C. by a vacuum laminator, and subsequently, the peeling layer at the side of the substrate layer was peeled, so that a laminate of the peeling layer, the pressure-sensitive adhesive layer, and the substrate layer was obtained. Next, the substrate layer and the protecting layer of the laminate were stuck to each other at a room temperature by the vacuum laminator, and subsequently, the peeling layer at the side of the protecting layer was peeled. In this manner, the laminate patchable to a living body 1 sequentially including the peeling layer 5, the pressure-sensitive adhesive layer 2, the substrate layer 3, and the protecting layer 4 was fabricated.

Examples 2 to 7

A protecting layer was fabricated in accordance with the mixing formulation described in Table 1, and subsequently, the laminate patchable to a living body 1 was fabricated in the same manner as that of Example 1.

Comparative Example 1

A laminate patchable to a living body of Comparative Example 1 was fabricated in the same manner as that of Example 1, except that the protecting layer 4 was not fabricated.

Evaluation (Chemical Resistance Test)

A cotton ball that was impregnated with a chemical (solvent, diethylene glycol monoethyl ether acetate (manufactured by Daicel Corporation), SP value ($SP_{solvent}$) of 9.0) was placed on the protecting layer of each of the laminates of Examples for 1 hour. Thereafter, the cotton ball was removed, and the surface thereof was observed. In the laminate of Comparative Example 1, the cotton ball was placed on the substrate layer.

The swelling condition of the surface of each of the laminates was observed, and the evaluation was carried out as follows. The results are shown in Table 1.

5: There was no change.
4: There was no change at 90% or more of the placement area.
3: There was no change at 80% or more and below 90% of the placement area.
2: There was a change in a range of above 20% of the placement area.
1: There was a change in the almost entire region of the placement area.

(Abrasion Resistance Test)

The abrasion properties of the protecting layer of each of the laminates of Examples, and the substrate layer of the laminate of Comparative Example were evaluated in conformity with JIS K 5600-5-4 (using Pencil Hardness B).

The abrasion condition of the surface of each of the laminates was evaluated as follows. The results are shown in Table 1.

5: No scar was recognized.
4: A slight scar was recognized
3: A small scar was recognized.
2: A deep scar was recognized.
1: The laminate was fractured.

TABLE 1

|  |  | Details | Ex. 1 | Ex. 2 | Ex. 3 | Ex. 4 | Ex. 5 | Ex. 6 | Ex. 7 | Comp. Ex. 1 |
| --- | --- | --- | --- | --- | --- | --- | --- | --- | --- | --- |
| Protecting Layer | PVA 10% Aqueous Solution (1) | VF-20 | 28.8 | — | — | 27.2 | 27.2 | 40.0 | — |  |
|  | PVA 10% Aqueous Solution (2) | PVA-117 | — | 28.8 | — | — | — | — | — |  |
|  | PVA 10% Aqueous Solution (3) | PVA-217 | — | — | 28.8 | — | — | — | — |  |
|  | Epoxy Resin | EXA-4850-150 | — | — | — | — | — | — | 40.0 |  |
|  | Cross-Linking Agent (1) | Blocked Isocyanate | 1.07 | 1.07 | 1.07 | — | — | — | — |  |
|  | Cross-Linking Agent (2) | Titanium Lactate | — | — | — | 1.09 | — | — | — |  |
|  | Cross-Linking Agent (3) | Bisvinylsulfone | — | — | — | — | 0.32 | — | — |  |
|  | Epoxy Curing Catalyst | Phenyl Imidazole | — | — | — | — | — | — | 0.4 |  |
|  | Surfactant | Polyether-Modified Silicone | 0.02 | 0.02 | 0.02 | 0.02 | 0.02 | — | — |  |
|  | Solvent | Water | 10.10 | 10.10 | 10.10 | 11.71 | 10.88 | — | — |  |
|  | $SP_{cover}$ Value |  | 12.8 | 12.8 | 12.8 | 13.6 | 12.9 | 12.6 | 11.0 |  |
| Substrate Layer | Substrate Resin | Polyether Urethane | 100 | 100 | 100 | 100 | 100 | 100 | 100 | 100 |
|  | Carboxylic Acid Ester | Glyceryl Tricaprylate | 10 | 10 | 10 | 10 | 10 | 10 | 10 | 10 |
| Pressure-Sensitive | Acrylic Polymer | iNA/MEA/AA = 65:30:5 | 100 | 100 | 100 | 100 | 100 | 100 | 100 | 100 |

TABLE 1-continued

| | | Details | Ex. 1 | Ex. 2 | Ex. 3 | Ex. 4 | Ex. 5 | Ex. 6 | Ex. 7 | Comp. Ex. 1 |
|---|---|---|---|---|---|---|---|---|---|---|
| Adhesive Layer | Carboxylic Acid Ester | Glyceryl Tricaprylate | 60 | 60 | 60 | 60 | 60 | 60 | 60 | 60 |
| | Cross-Linking Agent | Polyfunctional Isocyanate Compound | 0.01 | 0.01 | 0.01 | 0.01 | 0.01 | 0.01 | 0.01 | 0.01 |
| SP Difference | | $|SP_{cover} - SP_{solvent}|$ | 3.8 | 3.8 | 3.8 | 4.6 | 3.9 | 3.6 | 2.0 | — |
| Evaluation | | Chemical Resistance | 5 | 4 | 3 | 5 | 4 | 5 | 2 | 1 |
| | | Abrasion Resistance | 5 | 5 | 5 | 4 | 3 | 2 | 4 | 1 |

The numerical values in Table show parts by mass in each of the components. The details of the components described in Table 1 are shown as follows.

PVA 10% aqueous solution (1): 10 mass % aqueous solution of polyvinyl alcohol (trade name: "VF-20", manufactured by JAPAN VAM & POVAL CO., LTD., saponification degree of 97.7 to 98.5 mol %, polymerization degree of 2000, viscosity of 4 mass % aqueous solution (20° C.) of 35 to 45 mPa·s)

PVA 10% aqueous solution (2): 10 mass % aqueous solution of polyvinyl alcohol (trade name: "KURARAY POVAL PVA-117", manufactured by KURARAY CO., LTD., saponification degree of 98.0 to 99.0 mol %, polymerization degree of 1700, viscosity of 4 mass % aqueous solution (20° C.) of 25 to 31 mPa·s)

PVA 10% aqueous solution (3): 10 mass % aqueous solution of polyvinyl alcohol (trade name: "KURARAY POVAL PVA-217", manufactured by KURARAY CO., LTD., saponification degree of 87.0 to 89.0 mol %, polymerization degree of 1700, viscosity of 4 mass % aqueous solution (20° C.) of 20.5 to 24.5 mPa·s)

Epoxy resin: trade name: "EXA-4850-150", manufactured by DIC CORPORATION, modified product of bisphenol A Cross-linking agent (1): trade name: "SU-268A", manufactured by Meisei Chemical Work, Ltd., aqueous solution of blocked isocyanate (concentration of 44 mass %)

Cross-linking agent (2): trade name: "ORGATIX TC-315", manufactured by Matsumoto Fine Chemical Co., Ltd., water of titanium lactate/solution of propanol (concentration of 44 mass %)

Cross-linking agent (3): trade name: "VB-S", manufactured by FUJIFILM Corporation, N—N'-ethylenebis[2-(vinylsulfonyl)acetoamide], white powder Epoxy curing catalyst: trade name: "2PZ", manufactured by SHIKOKU CHEMICALS CORPORATION, 2-phenylimidazole Surfactant: trade name: "SILFACE SAG 002", manufactured by Nissin Chemical Industry Co., Ltd., polyether modified silicone iNA: isononyl acrylate MEA: methoxyethyl acrylate AA: acrylic acid While the illustrative embodiments of the present invention are provided in the above description, such is for illustrative purpose only and it is not to be construed as limiting the scope of the present invention. Modification and variation of the present invention that will be obvious to those skilled in the art is to be covered by the following claims.

INDUSTRIAL APPLICABILITY

The laminate patchable to a living body of the present invention can be applied in various industrial products, and can be, for example, used for various uses including medical use and sanitary material use.

DESCRIPTION OF REFERENCE NUMERALS

1 Laminate patchable to a living body
2 Pressure-sensitive adhesive layer
3 Substrate layer
4 Protecting layer
5 Peeling layer
6 Printed layer

The invention claimed is:

1. A laminate patchable to a living body, comprising:
a pressure-sensitive adhesive layer for patching to the living body,
a substrate layer disposed on a one-side surface in a thickness direction of the pressure-sensitive adhesive layer and supporting the pressure-sensitive adhesive layer, and
a protecting layer disposed on a one-side surface in a thickness direction of the substrate layer,
wherein the protecting layer is at least one selected from the group consisting of polyvinyl alcohol, a cross-linked product of the polyvinyl alcohol, a copolymer of the polyvinyl alcohol, and a modified product of the polyvinyl alcohol,
wherein the protecting layer is an outermost layer having an exposed surface on a one-side surface in a thickness direction of the protecting layer, the exposed surface being adapted to receive a printed layer, and
wherein the protecting layer is a chemical resistance layer, with respect to a chemical resistance of the protecting layer, the absolute value ($|SP_{cover} - SP_{solvent}|$) of a difference between the SP value ($SP_{cover}$) of the chemical resistance layer and the SP value ($SP_{solvent}$) of a solvent used for forming the printed layer is 1.0 or more and 7.0 or less, and the SP value is determined based on the Fedors method.

2. The laminate patchable to a living body according to claim 1, wherein
the protecting layer has at least one of chemical resistance and abrasion resistance, and the abrasion resistance is evaluated in conformity with JIS K 5600-5-4 (Scratch hardness (Pencil method), Pencil hardness B).

3. The laminate patchable to a living body according to claim 1, wherein the protecting layer has a thickness of 0.01 μm or more and 0.5 μm or less.

4. The laminate patchable to a living body according to claim 1, wherein the protecting layer has a thickness of 0.1 μm or more and 0.5 μm or less.

5. A laminate patchable to a living body, comprising:
a pressure-sensitive adhesive layer for patching to the living body,
a substrate layer disposed on a one-side surface in a thickness direction of the pressure-sensitive adhesive layer and supporting the pressure-sensitive adhesive layer, and
a protecting layer disposed on a one-side surface in a thickness direction of the substrate layer,
wherein the protecting layer is at least one selected from the group consisting of polyvinyl alcohol, a cross-linked product of the polyvinyl alcohol, a copolymer of the polyvinyl alcohol, and a modified product of the polyvinyl alcohol, and
wherein the protecting layer is an outermost layer having an exposed surface on a one-side surface in a thickness direction of the protecting layer, the exposed surface being adapted to receive a printed layer, and
wherein
the protecting layer is a chemical resistance layer,
with respect to a chemical resistance of the protecting layer, the SP value ($SP_{cover}$) of the chemical resistance layer is 12.0 or more and 16.0 or less, and the SP value is determined based on the Fedors method.

6. The laminate patchable to a living body according to claim 5, wherein
the protecting layer has at least one of chemical resistance and abrasion resistance, and the abrasion resistance is evaluated in conformity with JIS K 5600-5-4 (Scratch hardness (Pencil method), Pencil hardness B).

7. The laminate patchable to a living body according to claim 5, wherein the protecting layer has a thickness of 0.01 µm or more and 0.5 µm or less.

8. The laminate patchable to a living body according to claim 5, wherein the protecting layer has a thickness of 0.1 µm or more and 0.5 µm or less.

* * * * *